United States Patent [19]

Mösdorf et al.

[11] Patent Number: 4,968,808

[45] Date of Patent: Nov. 6, 1990

[54] PROCESS FOR THE PREPARATION OF NITROETHENE DERIVATIVES

[75] Inventors: Peter Mösdorf, Langenzenn; Helmut Schickaneder, Eckental; Kurt H. Ahrens, Nürnberg, all of Fed. Rep. of Germany

[73] Assignee: Heumann Pharma GmbH & Co., Nuremberg, Fed. Rep. of Germany

[21] Appl. No.: 176,757

[22] Filed: Apr. 1, 1988

[30] Foreign Application Priority Data

Apr. 6, 1987 [EP] European Pat. Off. ........ 87105064.7

[51] Int. Cl.$^5$ ................... C07D 277/28; C07D 307/52
[52] U.S. Cl. ...................................... 548/205; 549/495
[58] Field of Search .......................... 548/205; 549/495

[56] References Cited

U.S. PATENT DOCUMENTS

| | | | |
|---|---|---|---|
| 4,233,302 | 11/1980 | Smith | 548/205 |
| 4,760,075 | 7/1988 | Pioch | 548/205 |
| 4,777,260 | 10/1988 | Ryan | 548/205 |

FOREIGN PATENT DOCUMENTS

| | | | |
|---|---|---|---|
| 49618 | 4/1982 | European Pat. Off. | |
| 135803 | 4/1985 | European Pat. Off. | 548/205 |
| 224612 | 6/1987 | European Pat. Off. | 548/205 |
| 2423813 | 12/1974 | Fed. Rep. of Germany | |
| 2734070 | 2/1978 | Fed. Rep. of Germany | |

OTHER PUBLICATIONS

Rudchenko, Zh Org. Khim. 13, 1383 (1977) Abstract.
Buevich, Zh Org. Khim, 13, 2618 (1977) Abstract.

Primary Examiner—Robert Gerstl
Attorney, Agent, or Firm—Burns, Doane, Swecker & Mathis

[57] ABSTRACT

A new process for the preparation of the nitroethane derivatives, ranitidine and nizatidine, is described which takes place via intermediate products and enables the said compounds to be prepared with a higher degree of purity. Another advantage is that in contrast to the known processes, it is not accompanied by the liberation of the highly toxic and malodorous compound, methylmercaptan.

6 Claims, No Drawings

PROCESS FOR THE PREPARATION OF NITROETHENE DERIVATIVES

This invention relates to a new process for the preparation of nitroethene derivatives, in particular N-[2-[[[5-[(dimethylamino)methyl]-2-furanyl]methyl]thio]ethyl]-N'-methyl-2-nitro-1,1-ethenediamine and N-[2-[[[2-[(dimethylamino)methyl]-4-thiazolyl]methyl]thio]ethyl]-N'-methyl-2-nitro-1,1-ethenediamine and the physiologically acceptable salts thereof. These compounds, which are known as ranitidine (INN) and nizatidine (INN), have already been disclosed in DE-OS No. 2 734 070 and 3 521 456 and in EP specification No. 0 049 618.

The present invention also relates to the new compounds, 1-[2-[[[5-[(dimethylamino)methyl]-2-furanyl]methyl]thio]ethylamino]-2-nitro-1-phenoxyethene and 1-[2-[[[2-[(dimethylamino)methyl]-4-thiazolyl]methyl]thio]ethylamino]-2-nitro-1-phenoxyethene and their salts, which are intermediate products of the process according to the present invention.

Ranitidine and nizatidine are $H_2$-receptor blockers and are used in the treatment of gastric ulcers for inhibiting histamine-stimulated gastric acid secretion.

Various processes are already known for the preparation of ranitidine but those of industrial importance are mainly the reactions described in DE-OS Nos. 2 734 070 and 3 521 456 of 2-[[[5-[(dimethylamino)methyl]-2-furanyl]methyl]thio]ethylamine with N-methyl-1-methylthio-2-nitroetheneamine and the two-stage process of the reaction of 2-[[[5-(dimethylamino)methyl]-2-furanyl]methyl]thio]ethylamine, first with 1,1-bis-(methylthio)-2-nitroethene and then with methylamine.

According to EP specification No. 0 049 618, nizatidine is prepared by analogous processes from 2-[[[2-(dimethylamino)methyl]-4-thiazolyl]methyl]thio]ethylamine by a reaction with N-methyl-1-methylthio-2-nitroetheneamine or with 1,1-bis(methylthio)-2-nitroethene and methylamine.

It is an object of the present invention to provide a new and improved process for the preparation of ranitidine and nizatidine which in particular avoids the environmental pollution which is caused in the known processes by the release of methylmercaptan.

This problem is solved by the present invention.

The invention thus relates to a process for the preparation of nitroethene derivatives corresponding to the general formula I

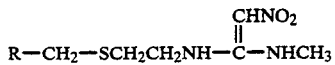

wherein R stands for the group

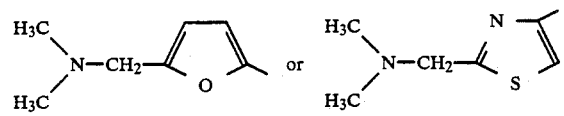

or the physiologically acceptable salts thereof, characterised in that (a) an amine corresponding to the general formula II

wherein R has the meaning indicated above is reacted with a compound corresponding to the general formula III

in which X stands for a halogen atom or an optionally substituted phenoxy group or with a compound corresponding to the general formula IV

wherein X has the meaning indicated above to produce an intermediate compound corresponding to the general formula V

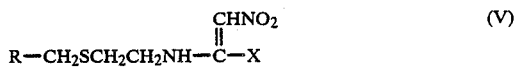

in which R and X have the meanings indicated above, (b) the resulting intermediate compound corresponding to the general formula V is reacted with methylamine to form a compound corresponding to the general formula I and (c) the resulting compound corresponding to the general formula I is optionally converted in known manner into a physiologically acceptable salt.

The process according to the invention is described in more detail below:

1. In the first step of the process according to the invention, an amine corresponding to the general formula II

wherein R has the meaning indicated above is reacted in a suitable solvent with a compound corresponding to the general formula III

in which X stands for a halogen atom or an optionally substituted phenoxy group or with a compound corresponding to the general formula IV

in which X has the meaning indicated above.

In the general formula III, the symbol X stands for a halogen atom, for example a chlorine or bromine atom, preferably a chlorine atom, or a phenoxy group which may be substituted. The substituents for the phenoxy group preferably consist of one or more, in particular one to three halogen atoms such as chlorine or bromine atoms, $C_1$ to $C_4$ alkyl groups, $C_1$ to $C_4$ alkoxy groups or nitro groups. Particularly preferred compounds corresponding to the general formula III are 1,1,1-trichloro-2-nitroethane(IIIa) and 1,1,1-triphenoxy-2-nitroethane(IIIb):

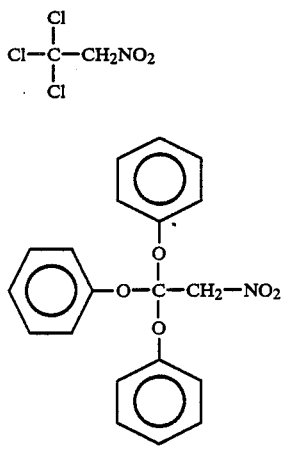

The preparation of the starting compounds corresponding to the general formula III is described, for example, by V. A. Buevich, N. Z. Nakova and V. V. Perekalin in Zh. Org. Khim. 15, 1473 (1979).

In the general formula IV, the symbol X carries the definition given for X in the compounds of the general formula III. 1,1-dichloro-2-nitroethene(IVa) and 1,1-diphenoxy-2-nitroethene(IVb) corresponding to the following structural formulae are particularly preferred starting compounds of the general formula IV:

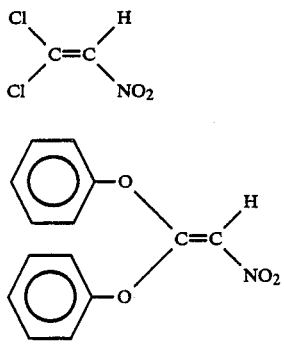

Examples of suitable solvents include ethers such as tetrahydrofuran or dioxane, ketones such as acetone, methylethyl ketone or 4-methyl-2-pentanone and acetonitrile. The reaction temperature is suitably maintained in a range from room temperature, e.g. 20° C., to the boiling point of the solvent used. The quantitative ratios of the starting compounds are in the range of from 2:1 to 1:1, preferably 1:1.

When X in the general formula III or the general formula IV stands for a halogen atom then it is advantageous to add an auxiliary base, for example a tertiary aliphatic amine such as triethylamine or a heterocyclic amine such as pyridine to the reaction mixture to bind the hydrohalic acid formed in the reaction. The auxiliary base may be added in one to two times the equimolar quantity.

The intermediate product corresponding to the general formula V obtained as described above may be isolated and purified by known methods and then reacted in a second stage to form the end product corresponding to formula I. Alternatively, isolation of the intermediate product of the general formula V may be omitted and the two reaction stages may be carried out together as a one shot process. This procedure is particularly preferred when the intermediate product of the general formula V is one in which X stands for a halogen atom.

1-[2-[[[5-(Dimethylamino)methyl]-2-furanyl]methyl]-thio]ethylamino]-2-nitro-1-phenoxyetbene corresponding to formula Va and 1-[2-[[[2-[(dimethylamino)methyl]-4-thiazolyl]methyl]-thio]ethylamino]-2-nitro-1-phenoxyethene corresponding to formula Vb, which are obtained as intermediate products in the first stage of the process according to the invention, are new compounds. They may also be prepared as acid addition products. These compounds and their baits are therefore also a subject of the present invention.

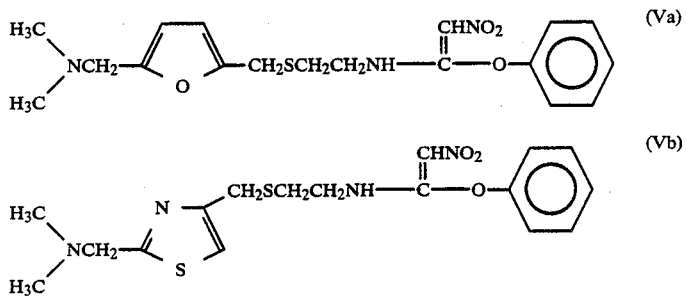

2. In the second stage of the process according to the invention, the compound corresponding to the general formula V is reacted with excess methylamine to be quantitatively converted into N-[2-[[[5-[(dimethylamino)methyl]-2-furanyl]-methyl]thio]ethyl]-N'-methyl-[2-nitro-1,1-ethenediamine or N-[2-[[[2-(dimethylamino)methyl]-4-thiazolyl]methyl]thio]ethyl]-N'-methyl-2-nitro-1,1-ethenediamine. The reaction is carried out in a solvent, for example an ether, an alcohol or water. Methanol, ethanol, isopropanol and n-butanol are examples of suitable alcohols. If an ether is used, this is preferably tetrahydrofuran or dioxane. The methylamine may be put into the reaction in the gaseous form or as a solution in the solvent used for the reaction and it is employed in excess, for example in a molar ratio of from 2:1 to 10:1, preferably 5:1, based on the intermediate product of the general formula V. The reaction temperature may lie in a range from 0° C. to the boiling point of the solvent used and is preferably from 20° to 30° C. The compounds of formula I prepared by this method may be isolated by commonly known methods such as crystallization from a suitable solvent, etc.

The compound of general formula I obtained in the second stage of the process according to the invention, i.e. ranitidine or nizatidine, may be converted into a physiologically acceptable salt thereof in known manner. The salt may be derived, for example, from a mineral acid such as hydrochloric, hydrobromic or hydriodic acid, phosphoric acid, metaphosphoric acid, nitric acid or sulphuric acid or it may be derived from an organic acid such as formic acid, acetic acid, propionic acid, phenyl acetic acid, tartaric acid, citric acid, fumaric acid, methane sulphonic acid, etc.

The compounds obtained by the process according to the invention may be formulated for administration in the same manner as already known for ranitidine and nizatidine and their salts, in particular their hydrochlorides.

The main advantages of the process according to the invention lie in the greater purity of the product obtained and above all in the ecologically improved conditions under which the process is carried out, that is to say that in contrast to the methods of preparation hitherto known for ranitidine and nizatidine, the process according to the invention is not accompanied by the formation of the highly toxic and malodorous compound, methylmercaptan.

The invention is illustrated in the Examples.

EXAMPLE 1

1-[2-[[[5-[(Dimethylamino)methyl]-2-furanyl]methyl]thio]ethylamino]-2-nitro-1-phenoxyethene.

21.4 g (0.1 mol) of 2-[[[5-[(dimethylamino)methyl]-2-furanyl]methyl]thio]ethylamine and 35.1 g (0.1 mol) of 1,1,1-triphenoxy-2-nitroethane are boiled for 3 hours in 250 ml of acetonitrile under a nitrogen atmosphere. The solvent is evaporated off under vacuum after cooling to 40° C. and the yellow oil left behind is chromatographed on 560 g of silica gel with dichloromethane/methanol (95:5). After concentration by evaporation under vacuum, the main fraction yields 28.7 g (76%) of the title compound in the form of a yellowish, viscous oil.

Rf (CH$_2$Cl$_2$/CH$_3$OH 95:5)=0.32

| $^1$H-NMR data (CDCl$_3$, TMS as internal standard) | δ = | 2.28 (s) 6 H, 2.83 (t) 2 H 3.45 (s) 2 H, 3.75 (t) 2 H, 3.80 (s) 2 H, 6.10–6.27 (m) 3 H, 7.08–7.63 (m) 5 H, 10.2 (broad) 1 H, replaceable by D$_2$O, ppm. |
|---|---|---|

EXAMPLE 2

N-[2-[[[5-[(Dimethylamino)methyl]-2-furanyl]methyl]thio]ethyl]-N'-methyl-2-nitro-1,1-ethenediamine hydrochloride.

45 ml (0.5 mol) of a solution of methylamine in methanol (11 mol/l) are added dropwise at room temperature to a solution of 37.7 g (0.1 mol) of 1-[2-[[[5-[(dimethylamino)methyl]-2-furanyl]methyl]thio]ethylamino]-2-nitro-1-phenoxyethene in 100 ml of methanol. After 3 hours' stirring, the solution is concentrated by evaporation under vacuum and the residue is taken up with 100 ml of ethanol. To the resulting solution are first added 25 ml of a solution of hydrogen chloride in ethanol (4 mol/l), and 125 ml of ethyl acetate are then slowly added. The precipitated hydrochloride is suction filtered, washed with 30 ml of ethyl acetate and dried under vacuum.

31.9 g (91%) of colourless crystals, m.p. 133° to 134° C.

EXAMPLE 3

N-[2-[[[5-[(Dimethylamino)methyl]-2-furanyl]methyl]thio]ethyl]-N'-methyl-2-nitro-1,1-ethene diamine (one shot process).

4.18 g (20 mmol) of 2-[[[5-[(dimethylamino)methyl]-2-furanyl]methyl]thio]ethylamine and 7.03 g (20 mmol) of 1,1,1-triphenoxy-2-nitro-ethane are stirred in 40 ml of 4-methyl-2-pentanone for 7 hours at 70° C.

After cooling to room temperature, 8 ml of a 40% solution of methylamine in water are added and the mixture is stirred for 4 hours. The water is then removed by azeotropic distillation and the solution left behind is cooled to 5° C. The resulting crystals are suction filtered and dried.

4.46 g (71%) of colourless crystals, m.p. 69° to 70° C.

EXAMPLE 4

N-[2-[[[5-[(Dimethylamino)methyl]-2-furanyl]methyl]thio]ethyl]-N'-methyl-2-nitro-1,1-ethene diamine (one shot process).

21.42 g (0.1 mol) of 2-[[[5-[(dimethylamino)methyl]-2-furanyl]methyl]thio]ethylamine and 14.0 ml (0.1 mol) of triethylamine in 100 ml of tetrahydrofuran are added dropwise at 3° to 5° C. to a solution of 17.85 g (0.1 mol) of 1,1,1-trichloro-2-nitroethane in 250 ml of tetrahydrofuran, the temperature being maintained by cooling with ice. After 2 hours' stirring in the ice bath, the reaction temperature is left to rise to 20° C. and 45 ml of a solution of methylamine in methanol (11 mol/l) are added dropwise. The reaction mixture is then stirred for 2 hours at room temperature and to a large extent evaporated under vacuum.

30 ml of a 30% sodium hydroxide solution and 150 ml of 4-methyl-2-pentanone are added to the residue. After phase separation, the aqueous solution is again extracted with 50 ml of 4-methyl-2-pentanone. The combined organic phases are dried by azeotropic distillation, treated with active charcoal, filtered and cooled to 5° C. 14.47 g (46%) of a beige coloured solid is obtained which thin layer chromatography shows to be identical to the compounds described above.

EXAMPLE 5

1-[2-[[[5-[(Dimethylamino)methyl]-2-furanyl]methyl]thio]ethylamino]-2-nitro-1-phenoxyethene.

A solution of 2.14 g (10 mmol) of 2-[[[5-[(dimethylamino)methyl]-2-furanyl]methyl]thio]ethylamine and 2.57 g (10 mmol) of 1,1-diphenoxy-2-nitroethene in 20 ml of acetonitrile is boiled for 2 hours. After concentration of the solution by evaporation under vacuum, the oily residue is chromatographically purified as described in Example 1 and yields 3.06 g (81%) of the title compound as a pale yellow oil which according to thin layer chromatography and $^1$H-NMR spectrum is identical to the compound from Example 1.

EXAMPLE 6

1-[2-[[[2-[(Dimethylamino)methyl]-4-thiazolyl]methyl]thio]ethylamino]-2-nitro-1-phenoxyethene.

2.31 g (10 mmol) of 2-[[[2-[(dimethylamino)methyl-4-thiazolyl]methyl]thio]ethylamine and 3.51 g (10 mmol)

of 1,1,1-triphenoxy-2-nitroethane in 30 ml of acetonitrile are boiled for 3 hours under a nitrogen atmosphere. The oil left behind after evaporation of the solvent under vacuum is chromatographed on silica gel with ethylacetate/methanol (95:5) as solvent. After concentration by evaporation under vacuum, the main fraction yields 3·51 g (89%) of the title compound as a pale yellow, viscous oil.

Rf (CH$_3$COOC$_2$H$_5$/CH$_3$OH 95:5): 0·36

| $^1$H-NMR data (CDCl$_3$, TMS as internal standard) | δ = | 2.34 (s) 6 H, 2.89 (t) 2 H, 3.78 (s) 2 H, 3.81 (t) 2 H, 3.90 (s) 2 H, 6.15 (s) 1 H, 7.10–7.68 (m) 6 H, 10.3 (broad) 1 H, replaceable by D$_2$O, ppm. |
|---|---|---|

EXAMPLE 7

N-[2-[[[2-[(Dimethylamino)methyl]-4-thiazolyl]methyl]thio]ethyl]-N'-methyl-2-nitro-1,1-ethene diamine.

3 ml of a solution of methylamine in methanol (11 mol/l) are added at room temperature to a solution of 2·37 g (6 mmol) of 1-[2-[[[2-[(dimethylamino)methyl]-4-thiazolyl]methyl]thio]ethylamino]-2-nitro-1-phenoxyethene in 10 ml of methanol and the mixture is stirred for 3·5 hours. The solution is then concentrated by evaporation under vacuum and 5 ml of ethyl acetate/ethanol (2:1) are added to the residue. After 10 minutes' stirring, the solid is separated by suction filtration and dried under vacuum. 2·99 g (90%) of colourless crystals, m.p. 131° to 132° C.

I claim:

1. Process for the preparation of nitroethene derivatives corresponding to the general formula I

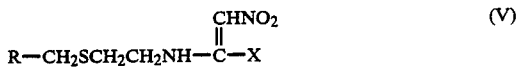

wherein R stands for the group

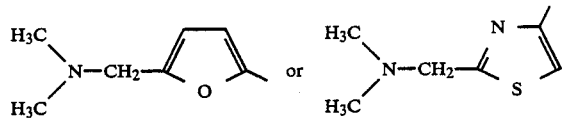

or of physiologically acceptable salts thereof, characterised in that
(a) an amine corresponding to the general formula II

R—CH$_2$SCH$_2$CH$_2$NH$_2$  (II)

wherein R has the meaning indicated above is reacted with a compound corresponding to the general formula III

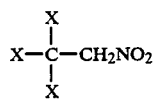

wherein X stands for a halogen atom or an optionally substituted phenoxy group to form an intermediate compound corresponding to the general formula V

R—CH$_2$SCH$_2$CH$_2$NH—C(=CHNO$_2$)—X  (V)

in which R and X have the meanings indicated above,
(b) the resulting intermediate compound corresponding to the general formula V is reacted with methylamine to form a compound corresponding to the general formula I
and optionally
(c) the resulting compound corresponding to the general formula I is converted into a physiologically acceptable salt in known manner.

2. Process according to claim 1 characterised in that the compound used as compound corresponding to the general formula III is 1,1,1-trichloro-2-nitroethane.

3. Process according to claim 1, characterised in that the compound used as compound corresponding to the general formula III is 1,1,1-triphenoxy-2-nitroethane.

4. Process according to claim 1, characterised in that stages (a) and (b) are carried out as a one pot process.

5. Process for the preparation of N-[2-[[[5-[(dimethylamino)methyl]-2-furanyl]methyl]thio ethyl]-N'-methyl-2-nitro-1,1-ethenediamine corresponding to the formula I

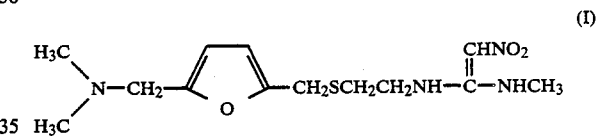

or of physiologically acceptable salts thereof, characterized in that
(a) an amine corresponding to the general formula II

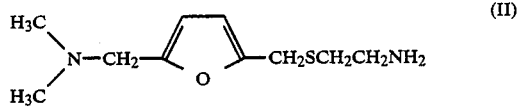

is reacted with 1,1,1-triphenoxy-2-nitroethane (III) to form an intermediate compound corresponding to the formula V

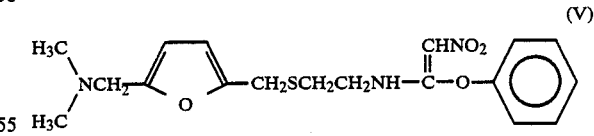

(b) the resulting intermediate compound corresponding to the formula V is reacted with methylamine to form a compound corresponding to the formula I
and optionally
(c) the resulting compound corresponding to the formula I is converted into a physiologically acceptable salt in known manner.

6. Process according to claim 5, characterized in that stages (a) and (b) are carried out as a one pot process.

* * * * *